(12) United States Patent
Wu et al.

(10) Patent No.: US 11,103,567 B2
(45) Date of Patent: Aug. 31, 2021

(54) GLYCOCONJUGATE VACCINES, PREPARATION METHOD AND USES THEREOF

(71) Applicant: Academia Sinica, Taipei (TW)

(72) Inventors: Shih-Hsiung Wu, Taipei (TW); Chung-Yi Wu, Taipei (TW); I-Ming Lee, Taipei (TW); Feng-Ling Yang, Taipei (TW)

(73) Assignee: ACADEMIA SINICA, Taipei (TW)

( * ) Notice: Subject to any disclaimer, the term of this patent is extended or adjusted under 35 U.S.C. 154(b) by 0 days.

(21) Appl. No.: 16/442,334

(22) Filed: Jun. 14, 2019

(65) Prior Publication Data

US 2020/0179503 A1    Jun. 11, 2020

Related U.S. Application Data

(60) Provisional application No. 62/775,938, filed on Dec. 6, 2018.

(51) Int. Cl.
| | | |
|---|---|---|
| A61K 39/05 | (2006.01) | |
| A61K 45/06 | (2006.01) | |
| A61P 31/04 | (2006.01) | |
| A61K 39/00 | (2006.01) | |

(52) U.S. Cl.
CPC ............. *A61K 39/05* (2013.01); *A61K 45/06* (2013.01); *A61P 31/04* (2018.01); *A61K 2039/6037* (2013.01); *A61K 2039/627* (2013.01)

(58) Field of Classification Search
CPC ................ A61K 39/05; A61K 45/06; A61K 2039/6037; A61P 31/04
USPC ................................................... 424/194.1
See application file for complete search history.

(56) References Cited

U.S. PATENT DOCUMENTS

2016/0193310 A1* 7/2016 Wong ................ A61K 49/00
                                                      424/9.1

FOREIGN PATENT DOCUMENTS

| TW | 200815028 A | 4/2008 |
| TW | 201817743 A | 5/2018 |
| TW | 201828978 A | 8/2018 |
| TW | 201834681 A | 10/2018 |

OTHER PUBLICATIONS

Huang et al. Microscale Nonreductive Release of O-Linked Glycans for Subsequent Analysis through MALDI Mass Spectrometry and Capillary Electrophoresis. Anal. Chem. 2001, 73, 6063-6069. (Year: 2001).*

Shen et al. Conjugation site modulates the in vivo stability and therapeutic activity of antibody-drug conjugates. Nature Biotechnology 30(2):184-189, 2012. (Year: 2012).*

Chusri et al. Impact of antibiotic exposure on occurrence of nosocomial carbapenem-resistant Acinetobacter baumannii infection: A case control study. J Infect Chemother 21 (2015) 90-95. (Year: 2015).*

Lee et al., "Pseudaminic Acid on Exopolysaccharide of Acinetobacter baumannii Plays a Critical Role in Phage-Assisted Preparation of Glycoconjugate Vaccine with High Antigenicity", Journal of the American Chemical Society, 2018, 140, 8639-8643.

Lee et al., "Structural basis for fragmenting the exopolysaccharide of Acinetobacter baumannii by bacteriophage ΦAB6 tailspike protein", Scientific Reports, 2017, 13 pages.

Zunk et al., "The occurrence and biological significance of the α-keto-sugars pseudaminic acid and legionaminic acid within pathogenic bacteria", Royal Society of Chemistry, 2014, 4, 3413-3421.

\* cited by examiner

*Primary Examiner* — Yih-Horng Shiao
(74) *Attorney, Agent, or Firm* — Birch, Stewart, Kolasch & Birch, LLP.

(57) ABSTRACT

Disclosed herein is a glycoconjugate vaccine conferring protection against a Gram negative pathogen infection, a method of manufacturing the glycoconjugate vaccine, and use of the glycoconjugate vaccine for treating bacterial infection. The glycoconjugate vaccine of the present disclosure has the structure of formula (I),

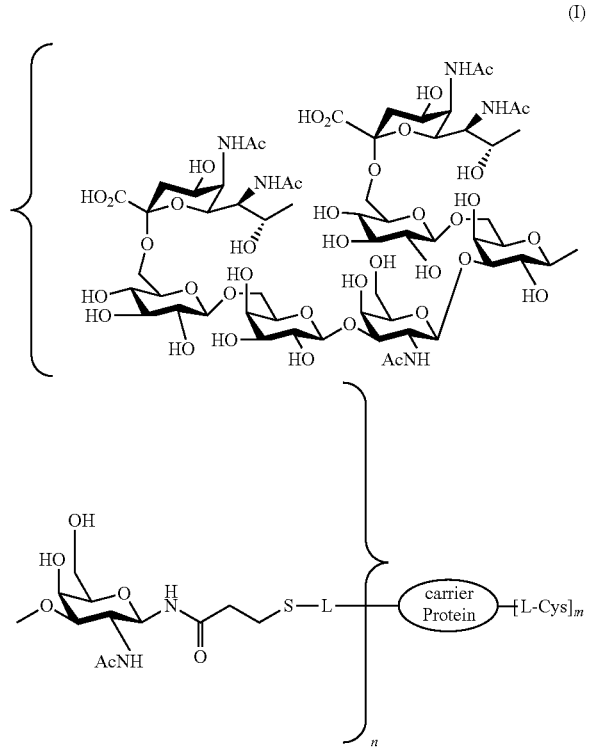

wherein, L is a maleimide-type linker, which is connected to the carrier protein via a maleimide bond formed therebetween; and n and m are independently an integral or a non-integral number between 2 and 20.

15 Claims, 5 Drawing Sheets

A 3x  9x  27x 81x  243x

B 3x  9x  27x 81x  243x

GLYCOCONJUGATE VACCINES, PREPARATION METHOD AND USES THEREOF

CROSS REFERENCES TO RELATED APPLICATION

This application claims the benefit of U.S. Provisional Application No. 62/775,938, filed Dec. 6, 2018, which is incorporated by reference herein in its entirety.

STATEMENT REGARDING PRIOR DISCLOSURES BY THE INVENTOR OR A JOINT INVENTOR UNDER 37 C.F.R. 1.77(B)(6)

Part of the subject matter of the invention described in the present application was published by the inventors, Shih-Hsiung Wu, Chung-Yi Wu, I-Ming Lee, and Feng-Ling Yang in an article entitled "Pseudaminic Acid on Exopolysaccharide of *Acinetobacter baumannii* Plays a Critical Role in Phage-Assisted Preparation of Glycoconjugate Vaccine with High Antigenicity." The article was published on Jul. 2, 2018 in J. Am. Chem. Soc. 140, 8639-8643. The publication was made by and/or originated from four members of the inventive entity of the present invention, and the entirety of this article is incorporated herein by reference. A copy of the article is provided in a concurrently filed Information Disclosure Statement pursuant to the guidance of 78 Fed. Reg. 11076 (Feb. 14, 2013)."

BACKGROUND OF THE INVENTION

1. Field of the Invention

The present disclosure in general relates to a glycoconjugate vaccine, which confers protection against a Gram-negative bacterial infection, and a method of producing the glycoconjugate vaccine.

2. Description of Related Art

Vaccines protect against a wide variety of infectious diseases. Many vaccines are produced by inactivated or attenuated pathogens which are injected into a subject, whereas others, so called 'subunit vaccines', are made from proteins or polysaccharides displayed on the surface of the pathogen. Subunit vaccines are preferred over inactivated or attenuated pathogens as they tend to cause fewer side effects.

The development and production of a subunit vaccine requires the identification and isolation of protective antigens front the pathogenic organism, and it has been recognized that the immunogenicity of polysaccharide antigens can be enhanced by conjugation to a protein carrier, m which bacterial polysaccharides are chemically bound to carrier proteins.

Glycoconjugate vaccines have been proven to be effective in combating a broad spectrum of diseases, particularly the infectious diseases caused by antibiotic resistant bacteria. In this regard, selection of targeted microbial exopolysaccharide (EPS) that elicits strong immune response with extensive strains coverage is prerequisite for glycoconjugate preparation. Furthermore, some earlier studies demonstrated that glycoconjugate with proper repeat units of EPS exhibited better bactericidal activity compared to those with whole EPS. However, using traditional chemical hydrolysis of EPS generated heterogeneous oligosaccharide fragments, which impede the reproducibility of glycoconjugate. Although, chemical synthesis of designed oligosaccharide could produce homogeneous oligosaccharides but was time consuming and had low yield.

We disclose a novel way of producing homogeneous oligosaccharide fragments of bacterial EPS, which allows the production of protective vaccines from the highly virulent wild-type strain of gram-negative bacteria, such as *Acinetobactor baumannii*, including the drug resistant strains. The glycoconjugate vaccine was easily prepared and was capable of providing significant protection against subsequent challenge, as well as killing the live bacteria.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

According to an aspect of the present disclosure, there is provided a glycoconjugate vaccine that confers protection against a Gram-negative bacterial infection in a subject. The glycoconjugate vaccine has the structure of formula (I),

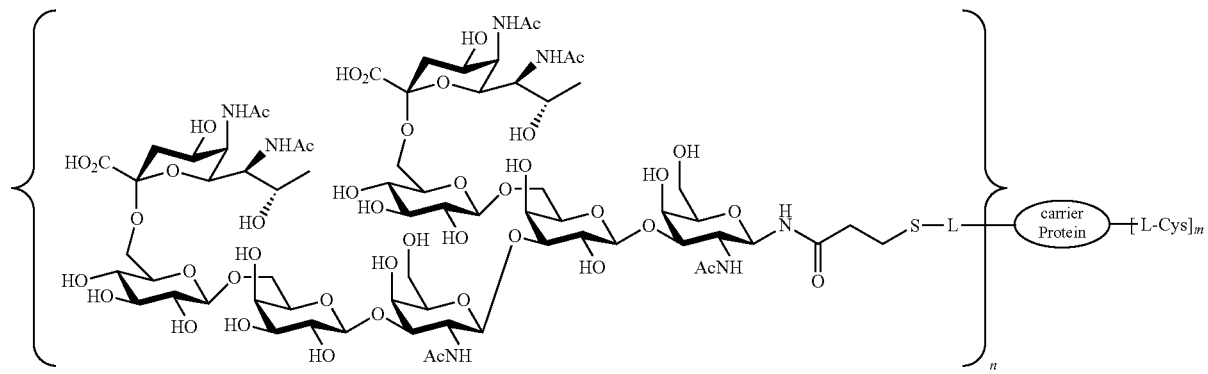

(I)

wherein,

L is a maleimide-type linker; and n and m are independently an integral or a non-integral number between 2 and 20.

According to embodiments of the present disclosure, in the formula (I), the maleimide-type linker may be selected from the group consisting of maleimidocaproyl (mc), maleimidomethyl cyclohexane-1-carboxylate (mcc), and succinimidyl 3-(bromoacetamido)propionate (SBAP).

According to embodiments of the present disclosure, in the formula (I), the carrier protein may be selected from the group consisting of diphtheria toxin (DT) mutant of *Corynebacterium diphtheriae* 197 (CRM197), exototxin A of *P. aeruginosa* (EPA), diphtheria toxoid, tetanus toxoid, detoxified hemolysin A of *S. aureus*, clumping factor A, *E. coli* heat labile enterotoxin, detoxified variants of *E. coli* heat labile enterotoxin, Cholera toxin B subunits (CTB), cholera toxin, detoxified variants of cholera toxin, *C. jejuni* AcrA, and *C. jejuni* natural glycoproteins.

According to one preferred embodiment of the present disclosure, in the formula (I), the maleimide-type linker is maleimidocaproyl, the carrier protein is the DT mutant CRM197, n is 4.8, and m is 16

According to optional embodiments, the glycoconjugate vaccine of formula (I) may further include an adjuvant.

According to another aspect of the present disclosure there is provided a method for the production of the present glycoconjugate vaccine of formula (I). The method includes steps of:

(a) digesting exopolysaccharides (EPS), isolated from a bacterium, with a phage tailspike protein (TSP) to produce an oligosaccharide 1;

(b) treating the oligosaccharide 1 with ammonium carbonate and subsequently with a sulfhydryl group introducing agent thereby generating an oligosaccharide 2 having a sulfhydryl group;

(c) coupling the oligosaccharide 2 to a carrier protein having a plurality of maleimide-type linkers via a maleimide reaction that occurred between the sulfhydryl group of the oligosaccharide 2 and the maleimide group of the plurality of maleimide-type linkers of the carrier protein; and (d) quenching the maleimide reaction of the step (c) by the addition of a sufficient amount of a cysteine thereby generating the glycoconjugate vaccine of formula (I);

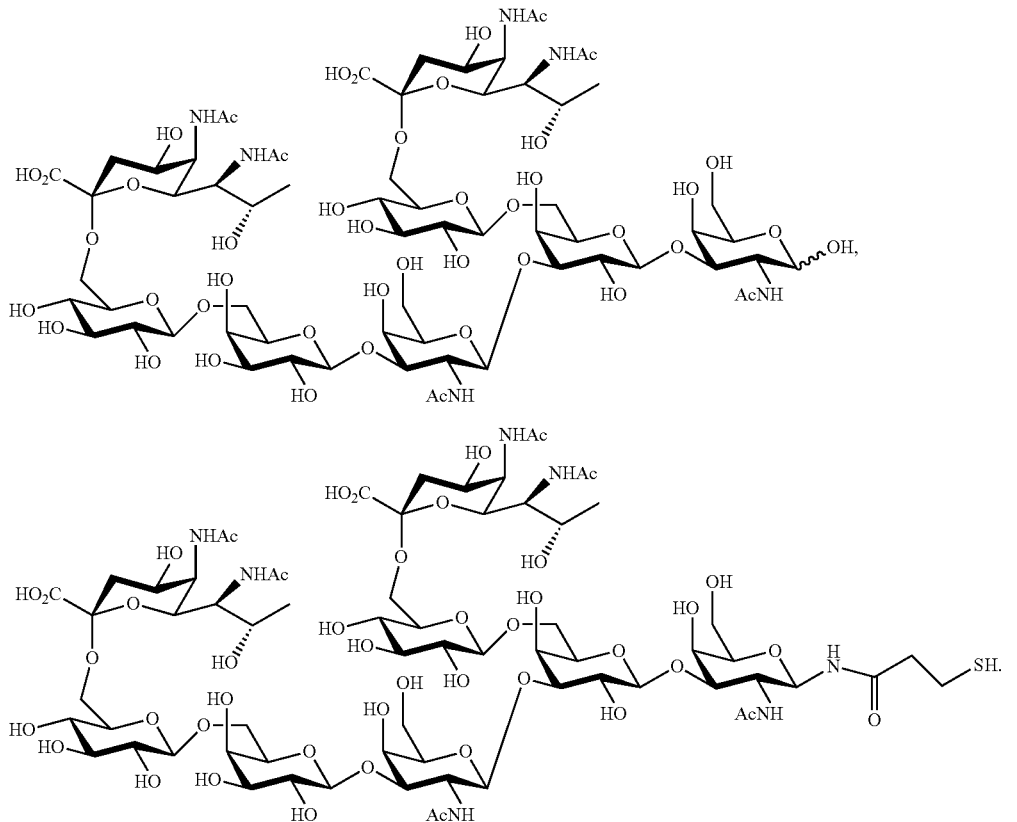

According to some embodiments of the present disclosure, in the step (a), the EPS is isolated from *Acinetobactor baumannii* strain 54149 (Ab-54149).

Examples of phage TSP suitable for use in the step (a) include, but are not limited to, phage AB6 TSP, phage P22 TSP, Phage SF6 TSP, Phage HK620 TSP, Phage T4 TSP and Phage T7 TSP. In one preferred embodiment, the EPS of Ab-54149 is digested with phage AB6 TSP to produce the oligosaccharide 1.

According to some embodiments of the present disclosure, in the step (b), the sulfhydryl group introducing agent is 3,3-dithiobis(sulfosuccinimidylpropionate) (DTSSP), dithiobis[succinimidylpropionate](DSP), 2-iminothiolane, N-succinimidyl S-acetylthioacetate (SATA), N-succinimidyl S-acetylthiopropionate (SATP), or SAT(PEG)$_4$.

According to embodiments of the present disclosure, in the formula (I), the maleimide-type linker is selected from the group consisting of maleimidocaproyl (mc), maleimidomethyl cyclohexane-1-carboxylate (mcc), and succinimidyl 3-(bromoacetamido)propionate (SBAP).

According to embodiments of the present disclosure, in the formula (I), the carrier protein is selected from the group consisting of diphtheria toxin (DT) mutant of Corynebacterium diphtheriae 197 (CRM197), exototxin A of P. aeruginosa (EPA), diphtheria toxoid, tetanus toxoid, detoxified hemolysin A of S. aureus, clumping factor A, E. coli heat labile enterotoxin, detoxified variants of E. coli heat labile enterotoxin, Cholera toxin B subunits (CTB), cholera toxin, detoxified variants of cholera toxin, C. jejuni AcrA, and C. jejuni natural glycoproteins.

According to preferred embodiments of the present disclosure, in the formula (I), the maleimide-type linker is maleimidocaproyl, the carrier protein is the DT mutant CRM197, n is 4.8, and m is 16.

According to a further aspect of the present disclosure, there is provided a method of protecting a subject from being infected by bacteria. The method includes the step of administering to the subject an effective amount of the present glycoconjugate vaccine of formula (I).

According to embodiments of the present disclosure, the bacteria may be any of Acinetobactor baumannii 54149, Actinoplanes utahensis VKM Ac-674, Aeromonas caviae UU51, Campylobacter jejuni 81-176, Campylobacter jejuni 11168, Campylobacter coli VC167, Cellulophaga funcicola, Escherichia coli O136, Helicobactor pylori 1061, Helicobactor pylori 26695, Helicobactor pylori 11687, Kribbella spp. VKM, Piscirickettsia salmonis, Proteus vulgaris O39, Pseudomonas aeruginosa O1a, Pseudomonas aeruginosa O7b, Pseudomonas aeruginosa O7d, Pseudomonas aeruginosa O9a, Pseudomonas aeruginosa O9b, Pseudomonas aeruginosa O10a, Pseudomonas aeruginosa PAO1, Pseudomonas aeruginosa PAM, Pseudomonas atlantica LAM 14165, Pseudomonas atlantica T9, Pseudoalteromonas distincta KMM 638, Rhizobium sp. NGR234, Shigella boydii type 7, Sinorhizobium fredii HH103, Sinorhizobium meliloti Rm1021, Vibrio cholera O:2, Vibrio vulnificus YJ016, or Vibrio vulnificus 27562. According to further embodiments of the present disclosure, the bacteria are drug resistant strains.

According to a further aspect of the present disclosure, there is provided a method of treating a bacterial infection in a subject. The method includes the step of administering to the subject an effective amount of the present glycoconjugate vaccine of formula (I).

According to embodiments of the present disclosure, the bacteria may be any of Acinetobactor baumannii 54149, Actinoplanes utahensis VKM Ac-674, Aeromonas caviae UU51, Campylobacter jejuni 81-176, Campylobacter jejuni 11168, Campylobacter coli VC167, Cellulophaga funcicola, Escherichia coli O136, Helicobactor pylori 1061, Helicobactor pylori 26695, Helicobactor pylori 11687, Kribbella spp. VKM, Piscirickettsia salmonis, Proteus vulgaris O39, Pseudomonas aeruginosa O1a, Pseudomonas aeruginosa O7b, Pseudomonas aeruginosa O7d, Pseudomonas aeruginosa O9a, Pseudomonas aeruginosa O9b, Pseudomonas aeruginosa O10a, Pseudomonas aeruginosa PAO1, Pseudomonas aeruginosa PAM, Pseudomonas atlantica LAM 14165, Pseudomonas atlantica T9, Pseudoalteromonas distincta KMM 638, Rhizobium sp. NGR234, Shigella boydii type 7, Sinorhizobium fredii HH103, Sinorhizobium meliloti Rm1021, Vibrio cholera O:2, Vibrio vulnificus YJ016, or Vibrio vulnificus 27562.

According to optional embodiments of the present disclosure, the method further includes the step of administering to the subject at least one anti-bacterial agent so as to ameliorate or alleviate the symptoms associated with the infection.

According to embodiments of the present disclosure, the anti-bacterial agent may be any of amoxicillin, ampicillin, azithromycin, clavulanic acid, cefuroxime, cefixime, cefpodoxime, ceftriaxone, doxycycline, luoroquinolones, macrolides, or moxifloxacin.

According to embodiments of the present disclosure, the subject is a human.

Many of the attendant features and advantages of the present disclosure will become better understood with reference to the following detailed description considered in connection with the accompanying drawings.

BRIEF DESCRIPTION OF THE DRAWINGS

The present description will be better understood from the following detailed description read in light of the accompanying drawings, where.

Figure 1:
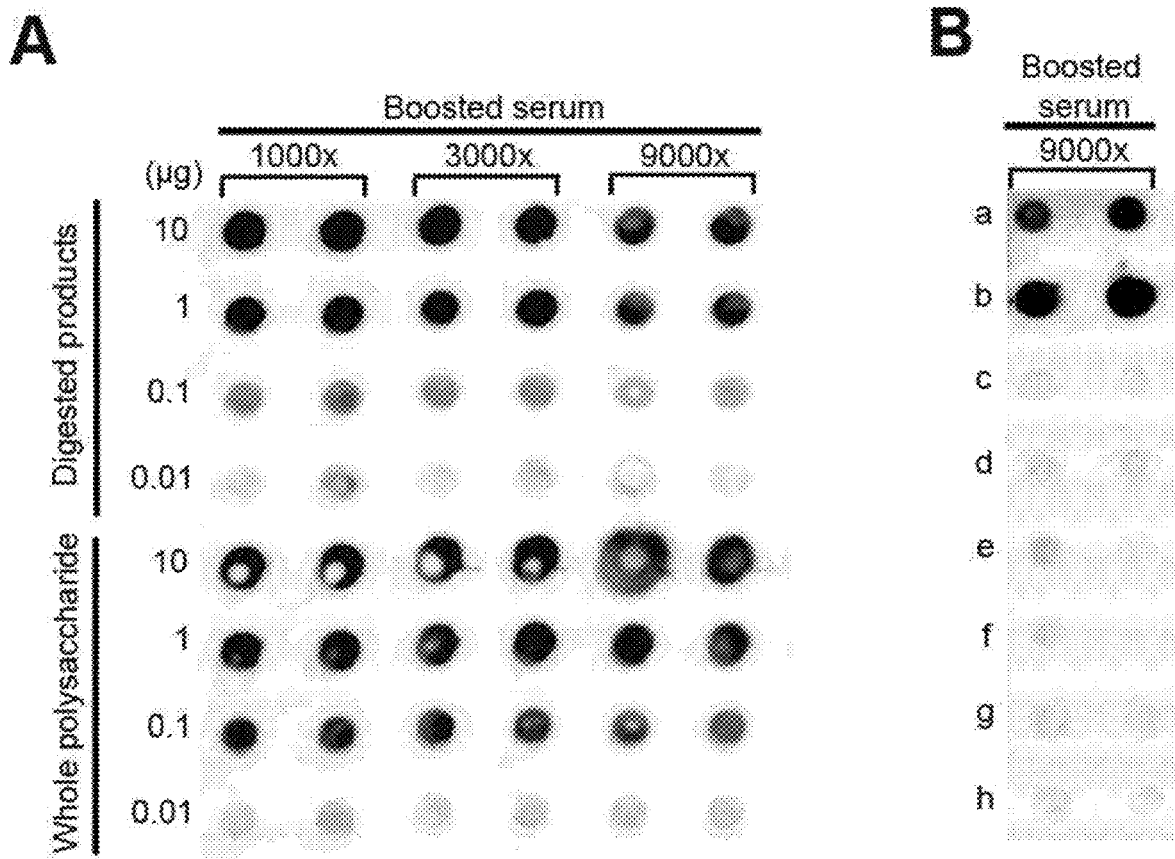
FIG. 1 depicts the cross-reaction of the serum boosted with the present glycoconjugate 3 against various strains of A. baumannii in accordance with one embodiment of the present disclosure. (A) A series of dilutions of the serum and varying amounts of the compound 1 and Ab-54149 EPS were tested. (B) Boosted serum with different bacterial exopolysaccharides. The carbohydrates used were as follows: a and b, the compound 1 and Ab-54149 EPS, respectively; c and d, the ΦAB2 TSP-digested products and Ab-SK44 EPS, respectively; e, f, g, and h, the whole extracts of EPS from Ab-SK17, K. pneumoniae K1,[6] K. pneumoniae K2,[6] and K. pneumoniae K64,[6] respectively. In all tests, the antiserum was diluted by 9000×, and the carbohydrates used were 10 μg.

*aeruginosa* bactericidal activity in serial dilutions (3× to 243×) of boosted serum evaluated by counting CFU on each agar plate.

DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

1. DEFINITIONS

For convenience, certain terms employed in the context of the present disclosure are collected here. Unless defined otherwise, all technical and scientific terms used herein have the same meaning as commonly understood by one of the ordinary skill in the art to which this invention belongs.

The term "adjuvant" as used herein refers to a substance which augments specific immune response to antigens by modulating the activity of immune cells. Examples of adjuvants include, but are not limited to, Freunds adjuvant, a bacterial cell wall derivative (e.g., muramyl dipeptide (MDP)), liposomes and etc. An adjuvant is therefore an immunomodulator.

The term "treatment" as used herein are intended to mean obtaining a desired pharmacological and/or physiologic effect, e.g., delaying or inhibiting the metastasis of a cancer. The effect may be prophylactic in terms of completely or partially preventing a disease or symptom thereof and/or therapeutic in terms of a partial or complete cure for a disease and/or adverse effect attributable to the disease. "Treatment" as used herein includes preventative (e.g., prophylactic), curative or palliative treatment of a disease in a mammal, particularly human; and includes: (1) preventative (e.g., prophylactic), curative or palliative treatment of a disease or condition (e.g., a cancer or heart failure) from occurring in an individual who may be pre-disposed to the disease but has not yet been diagnosed as having it; (2) inhibiting a disease (e.g., by arresting its development); or (3) relieving a disease (e.g., reducing symptoms associated with the disease).

The term "administered", "administering" or "administration" are used interchangeably herein to refer a mode of delivery, including, without limitation, intravenously, intramuscularly, intraperitoneally, intraarterially, intracranially, or subcutaneously administering an agent (e.g., the present glycoconjugate vaccine) that confers immunoprotection to a subject from a bacterial infection.

The term "an effective amount" as used herein refers to an amount effective, at dosages, and for periods of time necessary, to achieve the desired result with respect to the treatment of a bacterial infection. For example, in the treatment of a bacterial infection, an agent (i.e., the present glycoconjugate vaccine) which decrease, prevents, delays or suppresses or arrests the progression of bacterial infection would be effective in preventing bacteria from spreading to other locations and/or from growing. An effective amount of an agent is not required to cure a disease or condition but will provide a treatment for a disease or condition such that the onset of the disease or condition is delayed, hindered or prevented, or the disease or condition symptoms are ameliorated. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the like. Effective amount may be expressed, for example, as the total mass of the active agent (e.g., in grams, milligrams or micrograms) or a ratio of mass of the active agent to body mass, e.g., as milligrams per kilogram (mg/kg). The effective amount may be divided into one, two or more doses in a suitable form to be administered at one, two or more times throughout a designated time period.

The term "subject" or "patient" is used interchangeably herein and is intended to mean a mammal including the human species that is treatable by the compound of the present invention. The term "mammal" refers to all members of the class Mammalia, including humans, primates, domestic and farm animals, such as rabbit, pig, sheep, and cattle; as well as zoo, sports or pet animals; and rodents, such as mouse and rat. Further, the term "subject" or "patient" intended to refer to both the male and female gender unless one gender is specifically indicated. Accordingly, the term "subject" or "patient" comprises any mammal which may benefit from the treatment method of the present disclosure. Examples of a "subject" or "patient" include, but are not limited to, a human, rat, mouse, guinea pig, monkey, pig, goat, cow, horse, dog, cat, bird and fowl. In a preferred embodiment, the subject is a human.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The singular forms "a," "and," and "the" are used herein to include plural referents unless the context clearly dictates otherwise.

2. DETAIL DESCRIPTION OF PREFERRED EMBODIMENTS

The present disclosure is based, at least in part, on the unexpected discovery that glycoconjugates with proper repeat units of microbial exopolysaccharide (EPS) exhibited better bactericidal activity compared to those with whole EPS. Accordingly, one aspect of the present disclosure aims at providing a glycoconjugate vaccine that characterized in having homogeneous microbial oligosaccharide fragments covalently linked to a carrier protein. Other aspects of the disclosure include, at least, methods of producing the present glycoconjugate vaccine, and uses of the present glycoconjugate vaccine in conferring immunoprotection against a bacterial infection in a subject and/or treating a subject having a bacterial infection.

2.1 Glycoconjugate Vaccine

In one aspect, the present disclosure provides a glycoconjugate vaccine, which has the structure of formula (I), non-integral number between 2 and 20, such as 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2 m 9.3, 9.4, 9.5, 9.6, 9.7, 9.8, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 16.0, 16.1, 16.2, 16.3, 16.4, 16.5, 16.6, 16.7, 16.8, 16.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, and 20.0. In some embodiments, n is a non-integral number between 2 and 20 (e.g., 4.8); while m is an integral number between 2 and 20 (e.g., 16).

According to one preferred embodiment of the present disclosure, in the glycoconjugate vaccine of formula (I), the maleimide-type linker L is maleimidocaproyl, the carrier protein is the DT mutant CRM197, n is 4.8, and m is 16.

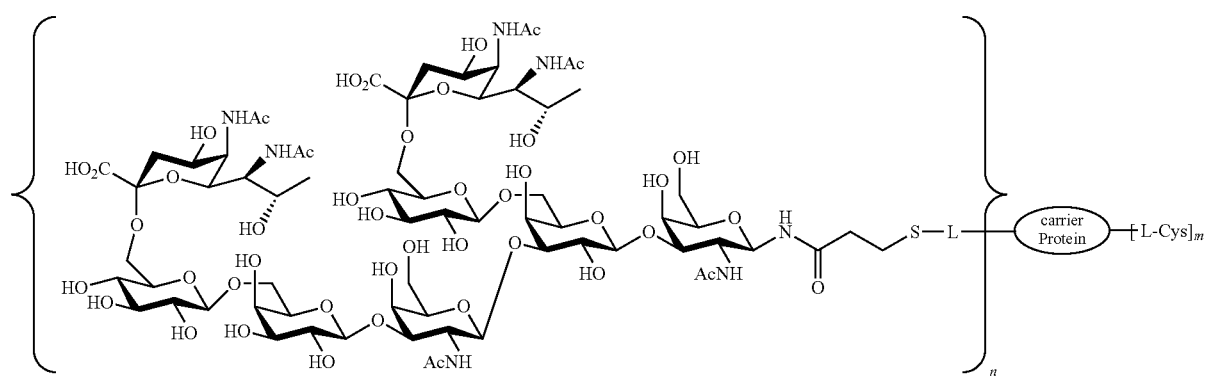

(I)

wherein,

L is a maleimide-type linker; and n and m are independently an integral or a non-integral number between 2 and 20.

In the formula (I), the maleimide-type linker (L) may be any of maleimidocaproyl (mc), maleimidomethyl cyclohexane-1-carboxylate (mcc), and succinimidyl 3-(bromoacetamido)propionate. Preferably, the maleimide-type linker (L) is maleimidocaproyl (mc).

The carrier protein may be selected from the group consisting of diphtheria toxin (DT) mutant of Corynebacterium diphtheriae 197 (CRM197), exototxin A of P. aeruginosa (EPA), diphtheria toxoid, tetanus toxoid, detoxified hemolysin A of S. aureus, clumping factor A, E. coli heat labile enterotoxin, detoxified variants of E. coli heat labile enterotoxin, Cholera toxin B subunits (CTB), cholera toxin, detoxified variants of cholera toxin, C. jejuni AcrA, and C. jejuni natural glycoproteins. Preferably, the carrier protein is (DT) mutant of CRM197.

According to embodiments of the present disclosure, in the formula (I), n and m are independently an integral or a According to optional embodiments, the glycoconjugate vaccine of formula (I) may further include an adjuvant. In some embodiments, the adjuvant is Freunds adjuvant. In other embodiments, the adjuvant is a bacterial cell wall derivative (e.g., muramyl dipeptide (MDP)).

2.2 Production of the Glycoconjugate Vaccine

According to another aspect of the present disclosure, there is provided a method for the production of the present glycoconjugate vaccine of formula (I), which is characterized in having homogeneous microbial oligosaccharide fragments covalently linked to a carrier protein. The method comprises steps of:

(a) digesting exopolysaccharides (EPS), isolated from a bacterium, with a phage tailspike protein (TSP) to produce an oligosaccharide 1;

(b) treating the oligosaccharide 1 with ammonium carbonate and subsequently with a sulfhydryl group introducing agent thereby generating an oligosaccharide 2 having a sulfhydryl group;

(c) coupling the oligosaccharide 2 to a carrier protein having a plurality of maleimide-type linkers via a maleimide reaction that occurred between the sulfhydryl group of the oligosaccharide 2 and the maleimide group of the plurality of maleimide-type linkers of the carrier protein; and (d) quenching the maleimide reaction of the step (c) by the addition of a sufficient amount of a cysteine thereby generating the glycoconjugate vaccine of formula (I);

of two repeat units of →3)-β-N-acetyl galactosamine (Gal-NAc)-(1→3)-[β-glucose (Glc)-(1→6)-β-galactose (Gal)-(1→, and each repeat units has a pseudaminic acid (Pse) connected to Glc via a Pse-(2→6)-α-Glc linkage.

For the purpose of constructing a vaccine, the bacterial antigen or the oligosaccharide 1 is modified to possess a

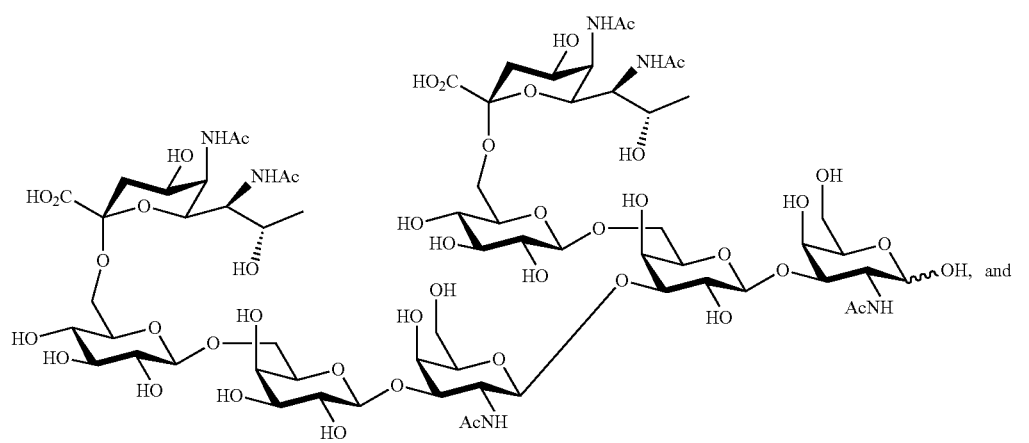

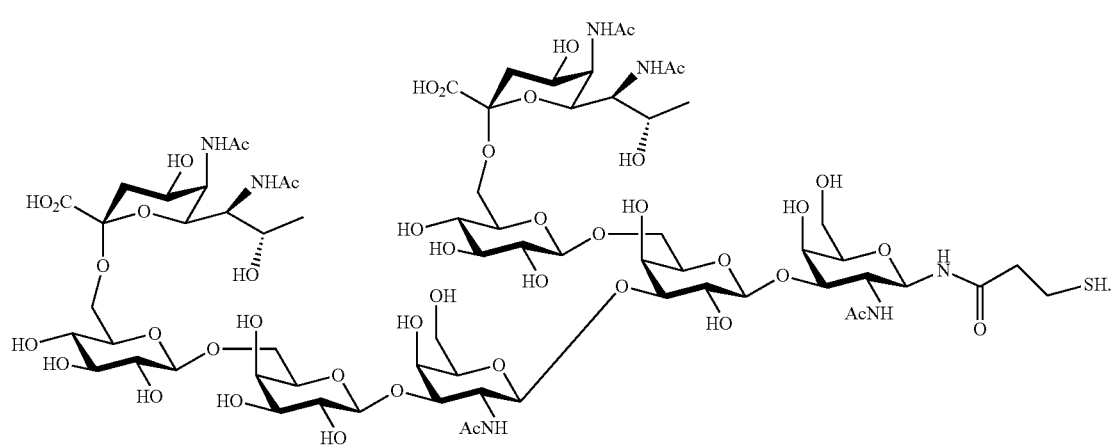

In general, the glycoconjugate vaccine described in Section 2.1 above is produced by connecting a microbial antigen, preferably a homogeneous microbial oligosaccharide of *A. baumannii*, to a carrier protein. To this purpose, in some embodiments of the present disclosure, EPS is first isolated from *Acinetobactor baumannii* strain 54149 (Ab-54149) by the method described in the working example of the present disclosure or by any method known to a skilled artisan. Then, the isolated Ab-54149 EPS is digested with a phage tailspike protein (TSP), so as to produce a homogeneous microbial oligosaccharide suitable for use as antigens. Examples of bacterial phage TSP suitable for use in the present method include, but are not limited to, phage AB6 TSP, phage P22 TSP, Phage SF6 TSP, Phage HK620 TSP, Phage T4 TSP and Phage T7 TSP. In one preferred example, Ab-54149 EPS is digested with phage AB6 TSP (ΦAB6TSP) and a homogeneous oligosaccharide 1 is produced (the step (a)). Note that in the step (a) of the present method, for the production of microbial antigens, it is not required to add a conventional chemical hydrolytic agent, such as an acid (e.g., acetic acid) or a base.

According to embodiments of the present disclosure, the oligosaccharide 1 thus produced in the step (a) is composed sulfhydryl group, while a carrier protein is modified to possess a maleimide group, so that they may be coupling together via a maleimide reaction that occurs between the sulfhydryl group of the bacterial antigen and the maleimide group of the carrier protein.

Accordingly, in the step (b), the oligosaccharide 1 is first treated with a saturated ammonium carbonate solution to convert the free hydroxyl group on the GalNAc ring into a primary amine, which is then reacted with a sulfhydryl group introducing agent, thereby generating an oligosaccharide 2 having a sulfhydryl group. Examples of the sulfhydryl group introducing agent suitable for use in the present method include, but are not limited to, 3,3-dithiobis(sulfosuccinimidylpropionate) (DTSSP), dithiobis[succinimidylpropionate] (DSP), 2-iminothiolane, N-succinimidyl S-acetylthioacetate (SATA), N-succinimidyl S-acetylthiopropionate (SATP), or SAT(PEG)$_4$. In one preferred embodiment, the sulfhydryl group introducing agent is DTSSP.

At the same time, a carrier protein is modified to include a plurality of maleimide-type linkers in its structure, in which each linkers possesses a maleimide group. Examples of maleimide-type linkers suitable for use in the present disclosure include, but are not limited to, maleimidocaproyl (mc), maleimidomethyl cyclohexane-1-carboxylate (mcc), and succinimidyl 3-(bromoacetamido)propionate (SBAP). In some preferred embodiments, a carrier protein is reacted with N-(ε-maleimidocarproyloxy)sulfosuccinimide ester (sulfo-EMCS) to produce a carrier protein having 21 maleimidocarproyl linkers in its structure. Examples of the carrier protein suitable for use in the present disclosure include, but are not limited to, diphtheria toxin (DT) mutant of *Corynebacterium diphtheriae* 197 (CRM197), exototxin A of *P. aeruginosa* (EPA), diphtheria toxoid, tetanus toxoid, detoxified hemolysin A of *S. aureus*, clumping factor A, *E. coli* heat labile enterotoxin, detoxified variants of *E. coli* heat labile enterotoxin, Cholera toxin B subunits (CTB), cholera toxin, detoxified variants of cholera toxin, *C. jejuni* AcrA, and *C. jejuni* natural glycoproteins. In some preferred embodiments, the carrier protein is DT mutant CRM197.

Then, in the step (c), the oligosaccharide 2 having a sulfhydryl group and the carrier protein having a plurality of maleimide-type linkers are covalently linked via a maleimide reaction that occurs between the sulfhydryl group of the oligosaccharide 2 and the maleimide group of the carrier protein. As the maleiminde groups on the carrier protein are in excess to the sulfhydryl groups of the oligosaccharide 2, thus, the maleimide reaction may be quenched by the addition of sufficient amount of cysteine, thereby generating the desired glycoconjugate vaccine (the step (d)).

According to preferred embodiments of the present disclosure, the glycoconjugate vaccine produced by the present method has the structure of formula (I), in which the maleimide-type linker is maleimidocaproyl, the carrier protein is the DT mutant CRM197, n is 4.8, and m is 16.

2.3 Use of the Glycoconjugate Vaccine 2.3.1 Method of Conferring Immunoprotection Against a Gram-Negative Bacterial Infection A further aspect of the present disclosure aims at providing a method of protecting a subject from a bacterial infection, particularly, an infection caused by gram-negative bacteria. The method includes the step of administering to the subject an effective amount of the present glycoconjugate vaccine of formula (I).

According to certain embodiments of the present disclosure, the present glycoconjugate vaccine of formula (I) is formulated with Freund's complete adjuvant, then the formulation is used to immunize test animals (i.e., rabbits). Sera collected from the immunized animals are rich in antibodies that exhibit immunogenicity towards both oligosaccharide 1 and Ab-54149 EPS. Further, the antibodies may specifically recognize EPS of the Ab-54149 strain only, and not EPS isolated from other strains of *A. baumannii* (e.g., Ab-SK44 and Ab-SK17).

Further, in certain embodiments of the present disclosure, in the case when Pse level on the EPS diminished (i.e., Ab-SK44 EPS), the sera collected from animals immunized with such antigens (EPS having low level of Pse) failed to recognize Ab-SK44 EPS, confirming the hypothesis that Pse may be the critical immunogenicity site. Accordingly, the present glycoconjugate vaccine of formula (I) having relatively higher level of Pse is useful for conferring immunoprotection against gram-negative bacteria selected from the group consisting of *Acinetobactor baumannii* 54149, *Actinoplanes utahensis* VKM Ac-674, *Aeromonas caviae* UU51, *Campylobacter jejuni* 81-176, *Campylobacter jejuni* 11168, *Campylobacter coli* VC167, *Cellulophaga funcicola*, *Escherichia coli* O136, *Helicobactor pylori* 1061, *Helicobactor pylori* 26695, *Helicobactor pylori* 11687, *Kribbella* spp. VKM, *Piscirickettsia salmonis*, *Proteus vulgaris* O39, *Pseudomonas aeruginosa* O1a, *Pseudomonas aeruginosa* O7b, *Pseudomonas aeruginosa* O7d, *Pseudomonas aeruginosa* O9a, *Pseudomonas aeruginosa* O9b, *Pseudomonas aeruginosa* O10a, *Pseudomonas aeruginosa* PAO1, *Pseudomonas aeruginosa* PA14, *Pseudomonas atlantica* LAM 14165, *Pseudomonas atlantica* T9, *Pseudoalteromonas distincta* KMM 638, *Rhizobium* sp. NGR234, *Shigella boydii* type 7, *Sinorhizobium fredii* HH103, *Sinorhizobium meliloti* Rm1021, *Vibrio cholera* O:2, *Vibrio vulnificus* YJ016, or *Vibrio vulnificus* 27562. Preferably, the bacteria are drug resistant strains.

2.3.2 Method of Treating a Gram-Negative Bacterial Infection

Another aspect of the present disclosure is directed to a method of protecting a subject from a bacterial infection, particularly, an infection caused by gram-negative bacteria. The method includes the step of administering to the subject an effective amount of the present glycoconjugate vaccine of formula (I).

According to certain embodiments of the present disclosure, the present glycoconjugate vaccine of formula (I) has the ability to kill live Ab-54149. Examples of the bacteria may be killed by the present glycoconjugate vaccine of formula (I) include, but are not limited to, *Acinetobactor baumannii* 54149, *Actinoplanes utahensis* VKM Ac-674, *Aeromonas caviae* UU51, *Campylobacter jejuni* 81-176, *Campylobacter jejuni* 11168, *Campylobacter coli* VC167, *Cellulophaga funcicola*, *Escherichia coli* O136, *Helicobactor pylori* 1061, *Helicobactor pylori* 26695, *Helicobactor pylori* 11687, *Kribbella* spp. VKM, *Piscirickettsia salmonis*, *Proteus vulgaris* O39, *Pseudomonas aeruginosa* O1a, *Pseudomonas aeruginosa* O7b, *Pseudomonas aeruginosa* O7d, *Pseudomonas aeruginosa* O9a, *Pseudomonas aeruginosa* O9b, *Pseudomonas aeruginosa* O10a, *Pseudomonas aeruginosa* PAO1, *Pseudomonas aeruginosa* PAM, *Pseudomonas atlantica* LAM 14165, *Pseudomonas atlantica* T9, *Pseudoalteromonas distincta* KMM 638, *Rhizobium* sp. NGR234, *Shigella boydii* type 7, *Sinorhizobium fredii* HH103, *Sinorhizobium meliloti* Rm1021, *Vibrio cholera* O:2, *Vibrio vulnificus* YJ016, or *Vibrio vulnificus* 27562. Preferably, the bacteria are drug resistant strains.

According to optional embodiments of the present disclosure, the method further includes the step of administering to the subject at least one anti-bacterial agent so as to ameliorate or alleviate the symptoms associated with the infection. The anti-bacterial agent may be administered to a subject prior to, together with, or after the administration of the present glycoconjugate vaccine of formula (I). Examples of anti-bacterial agent suitable for use with the present glycoconjugate vaccine of formula (I) include, but are not limited to, agent selected from the group consisting of amoxicillin, ampicillin, azithromycin, clavulanic acid, cefuroxime, cefixime, cefpodoxime, ceftriaxone, doxycycline, luoroquinolones, macrolides, and moxifloxacin.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent.

EXAMPLES

Materials and Methods

Extraction of *A. baumannii* exopolysaccharide (EPS). The crude extracts of bacterial surface polysaccharides were obtained based on the protocol reported by Zamze et al. (*J. Biol. Chem.* 2002, 277, 41613) with several modifications. In short, *A. baumannii* strain 54149 cells were cultured with LB medium at 37° C. for 15 h; then, the cultured cells were collected. The cells were suspended in distilled water and heated to 100° C. for 20 min to lyse the cells. The cell lysate was subjected to centrifugation at 10,000 rpm for 20 min, and the supernatant containing the bacterial surface polysaccharides was incubated with 80% acetone overnight to precipitate the polysaccharides. The precipitate was then dissolved in 10 mM Tris-HCl and 1 mM $CaCl_2$, pH 7.5, and further treated with ribonuclease (Sigma) and deoxyribonuclease I (Roche) at 37° C. for 6 h, followed by the treatment of proteinase K (Bioshop) for 12 hr. Subsequently, the sample was dialyzed against distilled water by using a 1 kDa-cutoff membrane and then lyophilized. Finally, the crude polysaccharide extracts were further purified by a HW-65F gel-permeation column (TSK-GEL) to remove any residual bacterial organisms. The presence and concentration of the extracted polysaccharides were determined by the phenol-sulfuric acid method.

Digestion of *A. baumannii* strain 54149 EPS by ΦAB6 TSP. 20 mg crude extract of Ab-54149 exopolysaccharide (Ab-54149 EPS) were dissolved in 25 mM Tris-HCl and 100 mM NaCl at pH 7.5 were incubated with 500 µg of purified ΦAB6 TSP at 37° C. for 6 h; then, the digestion reaction was terminated by heating to 100° C. for 15 min. The denatured proteins were removed by centrifugation. Subsequently, the crude oligosaccharides were loaded onto a P-6 column (Bio-Rad) and eluted with distilled water. The eluted fractions were pooled and lyophilized to obtain compound 1 (11 mg, 55% yield).

Mass spectrometry analysis. All mass spectrometry in this study were executed by ESI-MS and ESI-MS-MS. ESI-MS and ESI-MS-MS analyses were done on a LTQ Orbitrap XL ETD mass spectrometer (Thermo Fisher Scientific, San Jose, Calif.) equipped with standard ESI ion source. For the analysis, 5 µL of sample was injected at a flow rate of 50 µL/min in 80% $ACN/H_2O$ with 0.1% FA by Ultimate 3000 RSLC system from Dionex (Dionex Corporation, Sunnyvale, Calif.). The conditions for full-scan MS are as follows: mass range from 0 to 6000 m/z, and resolution was 60,000 at m/z 400. The target ions were sequentially isolated for MS2 by LTQ. Electrospray voltage was maintained at 4 kV and capillary temperature was set at 275° C.

Dot-blot analysis. After formulated with the Freund's complete adjuvant, the glycoconjugates 3 were used to immunize rabbits via subcutaneous injection. On days 14, 28, and 42, the rabbits were further boosted with the glycoconjugates, and the boosted serum was collected on day 49. For dot blot assay, 100 µL of the compound 1 or whole polysaccharides was deposited on a PVDF membrane using the Bio-dot microfiltration apparatus (Bio-Rad). The membrane was air-dried for 5 min and then blocked with 5% skimmed milk in PBS added 0.1% Tween 20 (PBST) at room temperature for 1 h. Subsequently, the membrane was incubated with the boosted serum at room temperature for 1 h. The membrane was washed with PBST and then incubated with the HRP-conjugated anti-rabbit IgG antibody (GE Healthcare) for 1 h. Finally, the membrane was washed with PBST again and the immuno-reactive dots were visualized by using the reagent enhanced chemiluminescence (Millipore).

Flow cytometry. Bacteria Ab-54149 were grown in LB medium overnight and then diluted to $10^6$ CFU. The diluted bacteria were incubated with 100-diluted (PBS, 1% BSA) glycoconjugate 3 boosted serum for 1 hour in ice. After washing with PBS, the bacteria were incubated with secondary anti-rabbit Alexa Fluor 488-labeled antibodies (Thermo Fisher; 1:400 diluted in PBS with 1% BSA) for 1 hour in ice. After further washing, the bacteria were resuspended in 2 mL PBS and then analyzed by MoFlo XDP flow cytometer (Beckman Coulter). The bacteria incubated with secondary antibodies were only used as negative control.

Serum bactericidal assay. Bacteria Ab-54149 was grown in the LB medium overnight and then diluted to 1:60000 in PBS to approximately $10^4$ CFU/mL. The bacterial sample was distributed into sterile polystyrene 96-well titer plates with 10 µL in each well. The glycoconjugate 3 boosted serum was serially diluted 3-fold (1/3 to 1/729) with PBS, and then 20 µL serum was added into the bacterial suspension for incubation of 15 minutes at 37° C. Serum was heated at 56° C. for 30 minutes to inactivate endogenous complement. After incubation, 30 µL of newborn rabbit complement (BRC) (Bio-Rad) was added to each well, and the sample was incubated at 37° C. for 1.5 hours. Negative controls were comprised of Ab-54149 and BRC only. Each sample and control was tested in triplicate. A 5 µL reaction mixture from each well was spotted onto the LB agar plate and subsequently incubated at 37° C. overnight. Resulting CFU were counted on the following day to determine the bactericidal activity. Subtraction CFU of 1/3 diluted serum from CFU of negative control was set to 100% bacterial death and the bacterial death percentage of other diluted serum was evaluated by the same strategy.

Example 1 Production of the Present Glycoconjugate

The present glycoconjugate was produced in accordance with Scheme I.

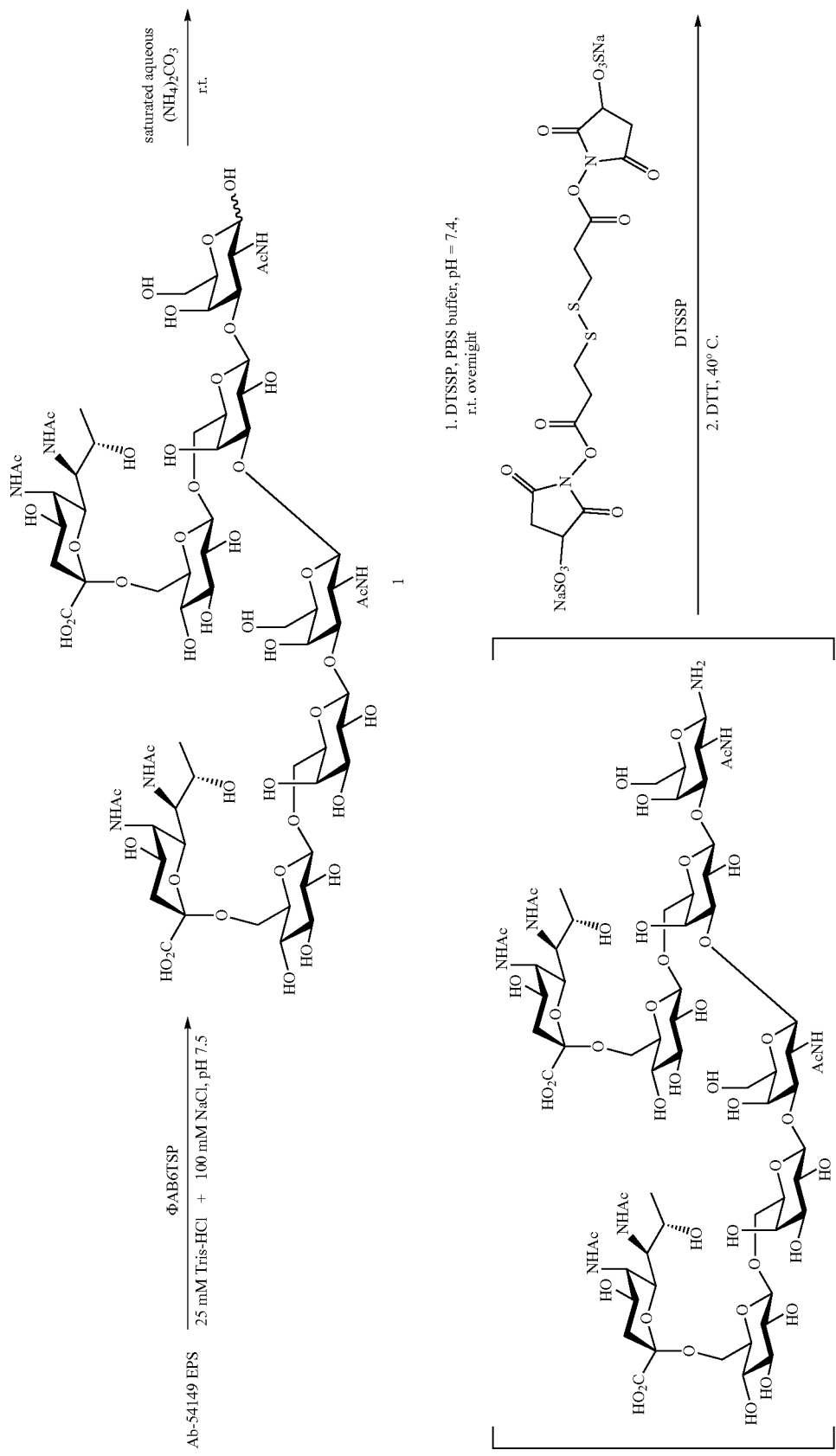

-continued
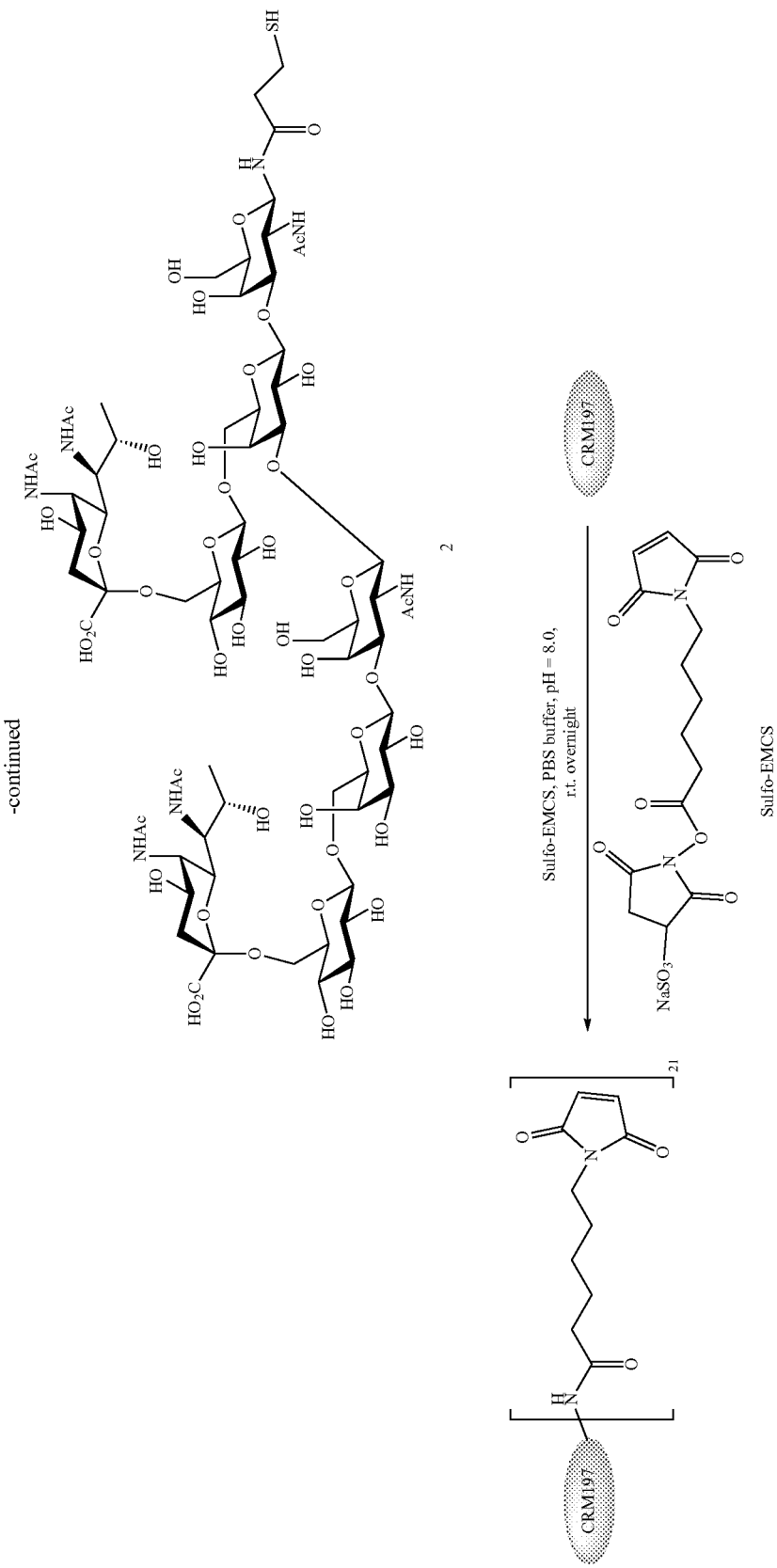

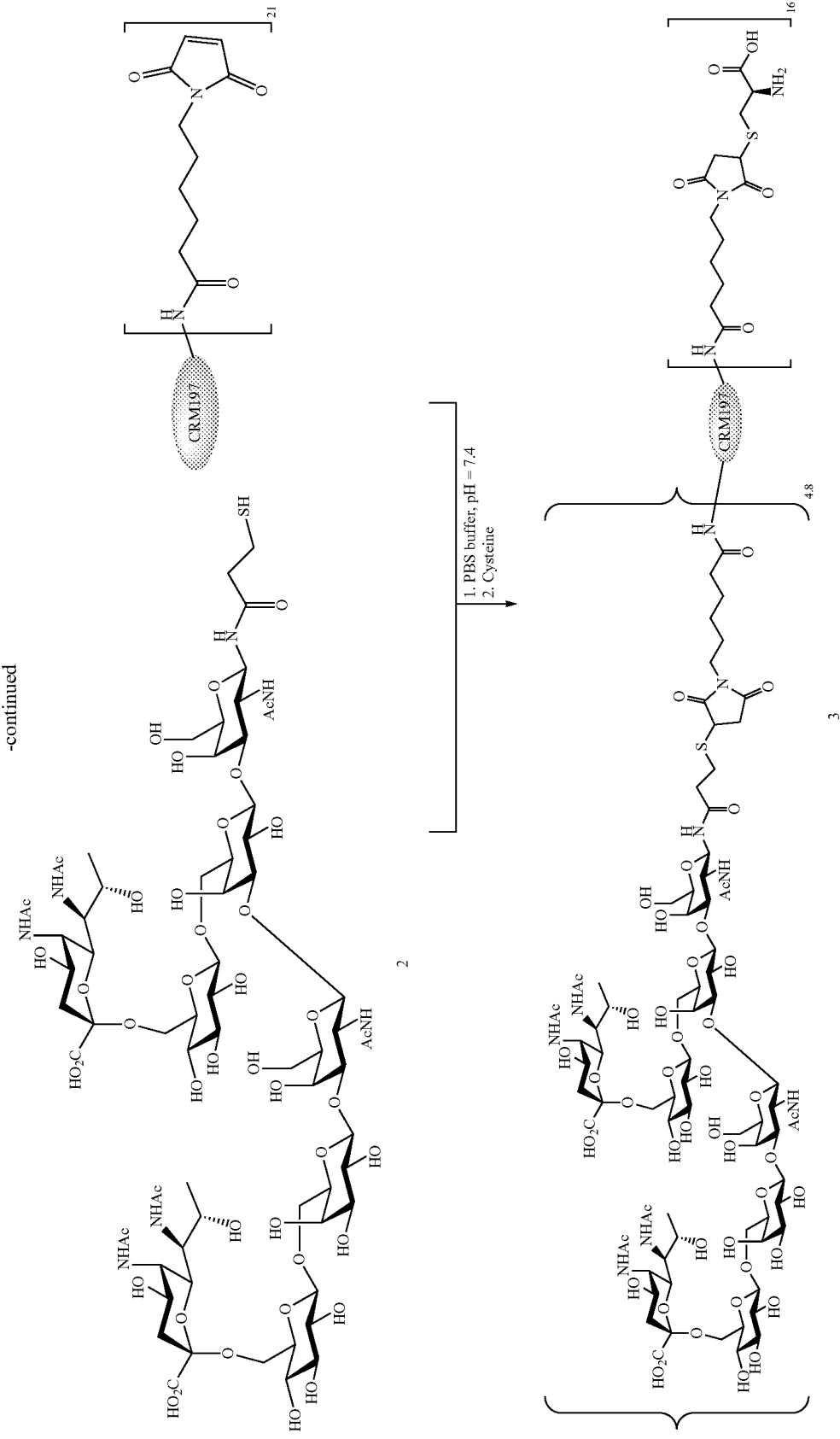

1.1 Preparation of Compound 1

To produce microbial oligosaccharide fragments, microbial expopolysaccharide (EPS) was first extracted from the cell walls of Acinetobacter baumannii strain 54149 (Ab-54149). The extracted EPS was found to composed of a repeat unit of →3)-β-N-acetyl galactosamine (GalNAc)-(1→3)-[β-glucose (Glc)-(1→6)]-β-galactose (Gal)-(1→ and majority of the repeat unit contained a pseudaminic acid (Pse) connected to Glc via a Pse-(2→6)-α-Glc linkage. Then, the extracted Ab-54149 EPS was fragmented by subjecting to the digestion of a phage ΦAB6 tailspike protein (ΦAB6TSP) in accordance with procedures described in the section of "Materials and Methods." A homogeneous oligosaccharide compound 1 (11 mg, 55% yield) containing two repeat units was produced, and analyzed by MS and NMR.

Compound 1 $^1$H NMR (500 MHz, D$_2$O): δ 4.74-4.71 (m, 1H), 4.6-4.39 (m, 4H), 4.25-4.09 (m, 12H), 4.08-3.89 (m, 13H), 3.85-3.75 (m, 9H), 3.74-3.40 (m, 12H), 3.25-3.18 (m, 2H), 2.11-2.04 (m, 2H), 1.98-1.88 (m, 18H), 1.56-1.48 (m, 2H), 1.09 (s, 3H), 1.08 (s, 3H); $^{13}$C NMR (150 MHz, D$_2$O): δ=174.77, 174.64, 173.72, 104.70, 103.51, 102.89, 100.44, 79.62, 75.34, 74.74, 73.68, 73.18, 72.39, 70.48, 69.80, 69.25, 68.51, 68.04, 66.87, 64.85, 62.24, 61.05, 59.39, 53.62, 51.42, 48.67, 35.20, 22.26, 22.07.

1.2 Preparation of Compound 2

Ammonium carbonate (3.0 g, excess) was added into a solution of compound 1 (20 mg) in 3.0 mL of distilled water. The resulting suspension was sealed, and stirred at room temperature for 7 days. The reaction mixture was freeze-dried until the dry weight of the residue remains constant. These glycosyl amines were obtained as colourless solids and used without further purification to react with 3,3'-Dithiobis(sulfosuccinimidyl-propionate) (DTSSP) (1.0 eq.) in pH 7.4 PBS buffer at room temperature overnight. Initially, the pH value of the reaction was adjusted by 1N NaOH(aq) and 1N HCl every 20 minutes for three times to keep around 7. Dithiothreitol (DTT) (1.0 mg) was added into the solution for another 2 hours of reaction at 40° C. Afterward, the material in the solution was loaded into Sephadex LH-20 column for purification to obtain the thiol product compound 2 (8.8 mg, yield 41.9% over 3 steps).

compound 2 $^1$H NMR (600 MHz, CDCl$_3$): δ 4.74-4.71 (m, 1H), 4.55-4.49 (m, 4H), 4.34-4.16 (m, 12H), 4.12-3.85 (m, 13H), 3.85-3.70 (m, 9H), 3.68-3.48 (m, 12H), 3.33-3.30 (m, 2H), 2.90-2.57 (m, 4H, linker CH$_2$—CH$_2$), 2.19-2.16 (m, 2H), 2.07-2.00 (m, 18H), 1.65-1.60 (m, 2H), 1.20 (s, 3H), 1.19 (s, 3H); $^{13}$C NMR (150 MHz, CDCl$_3$): δ=175.25, 175.09, 174.95, 174.83, 174.78, 174.65, 173.72, 104.70, 103.51, 102.90, 100.44, 81.63, 80.20, 79.62, 78.44, 76.55, 75.35, 74.74, 74.69, 73.68, 73.18, 72.40, 70.56, 70.48, 69.98, 69.75, 69.24, 69.17, 68.60, 68.49, 68.02, 66.85, 64.86, 62.25, 61.07, 60.99, 53.62, 51.42, 48.67, 39.38 (linker, CH$_2$), 35.20, 22.34, 22.26, 22.09, 22.07, 21.95, 19.61 (linker, CH$_2$), 15.77.

1.3 Preparation of CRM197-Maleimide

One mg/mL carrier protein CRM197 (Diphtheria toxin mutant) and 1 mL N-(ε-maleimido-caproyloxy)sulfosuccinimide ester (sulfo-EMCS) were mixed in pH 8.0 PBS buffer and gently stirred at room temperature for 2 hours. The mixture was then diluted with distilled water and centrifuged against 4 changes of deionized water by Ami con Ultra-0.5 10 KDa. The protein solution concentration was determined by nanodrop (0.97 mg/mL, total volume 1 mL) and lyophilized to obtain CRM197-maleimide (0.97 mg) of which the maleimide incorporation number can be determined by MALDI-TOF (positive mode, sinapinic acid matrix, water). The maleimide was conjugated to CRM197 in an average number of 21.

1.4 Conjugation of Compound 2 with CRM197-Maleimide to Obtain Glycoconjugate 3

CRM197-maleimide of Example 1.3 (conc. 0.97 mg/mL, total 0.980 mL) was dissolved in pH 8.0 PBS. Then, compound 2 (1.1 mg) was added in the molar ratio of 1:40. The subsequent procedure was the same as the method of CRM197-maleimide preparation. Finally, 1 mg cysteine was added to quench excess maleimide group. Again, the compound 1 incorporation number on glycoconjugate 3 was determined by MALDI-TOF. The conjugation yield is 93% based on the protein concentration.

Example 2 Animal Immunization Studies

In this example, the glycoconjugates of Example 1 were formulated with the Freund's complete adjuvant and were then used to immunize rabbits with 4 times boosting in 2 weeks interval in accordance with procedures described in the "Materials and Methods" section; and sera were collected for dot blot analysis. Results are illustrated in FIGS. 1 to 2.

It was found that boosted sera from the rabbits could recognize both Ab-54149 EPS and compound 1, indicating an excellent immunogenicity of the compound 1 (FIG. 1, panel A). Notably, boosted serum was sensitive toward Ab-54149 EPS than compound 1. Moreover, the dot blot results suggested that Ab-54149 EPS-induced and glycoconjugate 3 boosted antibodies aimed at similar antigen because both antibodies were able to recognize Ab-54149 EPS and compound 1. Hence, it was speculated that glycoconjugate 3 boosted sera might exhibit broad coverage with EPS from other 250 A. baumannii clinical strains like Ab-54149 EPS-induced antibodies. However, the boosted sera exhibited weak cross-reaction on different EPS from other A. baumannii strains and bacteria, suggesting its high specificity on Ab-54149 EPS (FIG. 1, panel B). FIG. 1, panel B, lanes c to h depicts results from Ab-SK44, Ab-SK17, K. pneumoniae K1, K. pneumoniae K2, and K. pneumoniae K64.

Figure 2:
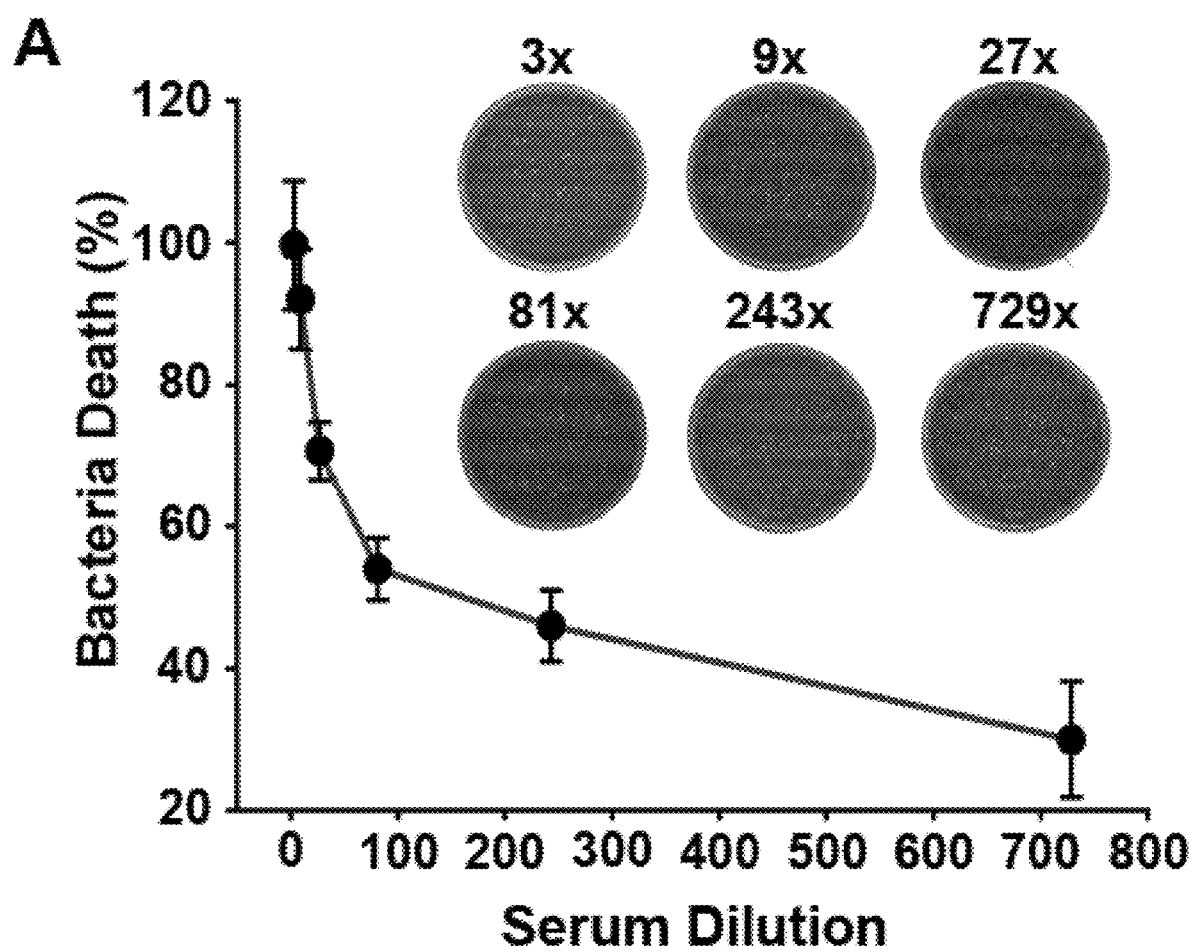
FIG. 2 depicts the bacterial cell killing and cross-reacting ability of the present glycoconjugate 3 boosted serum in accordance with one embodiment of the present disclosure. (A) Complement bactericidal activity in serial dilutions (3× to 729×) of boosted serum. Percentage of bacterial death is evaluated by counting CFU on each agar plate (the insert). Data are mean±standard deviation from three independent experiments. (B) 3,000× diluted serum reacted with various amount of Ab-54149 EPS, de-Pse Ab-54149 EPS, compound 1 and de-Pse compound 1, respectively. (C) On the left panel, 3000× diluted serum react with Pse releasing from Ab-54149 EPS over time (acetic acid hydrolysis for 40, 80 and 120 minutes) and Ab-54149 EPS. Pse from hydrolysis for 120 minutes and Ab-54149 EPS were quantified to 10 μg. Concentration of a line was 10 times higher than b line. On the right panel, 3000× diluted serum was treated with 10 μg and 1 μg sialic acid, GalNAcp, Galp and Glcp, respectively.
Figure 2:
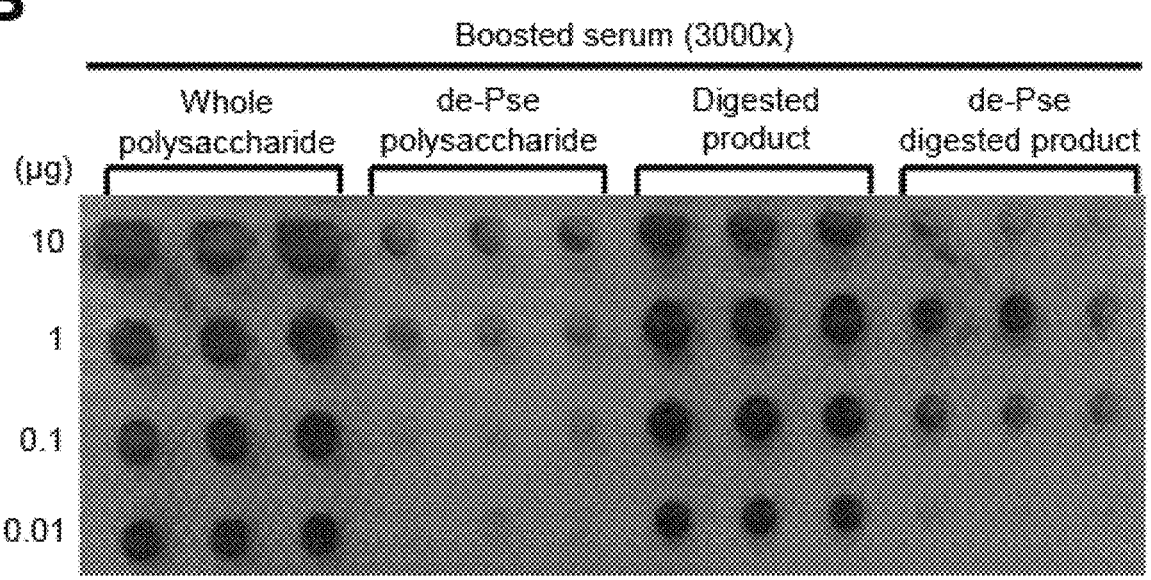
Figure 2:
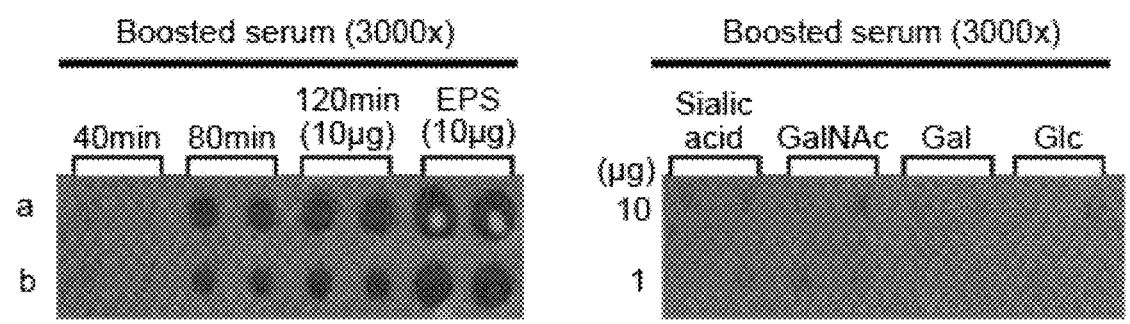
Figure 3:
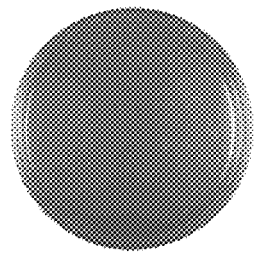
FIG. 3 depicts the bacterial cell killing and cross-reacting ability of the present glycoconjugate 3 boosted serum in accordance with one embodiment of the present disclosure. (A) Complement H. pylori bactericidal activity in serial dilutions (3× to 243×) of boosted serum evaluated by counting CFU on each agar plate. (B) Complement P.
Figure 3:
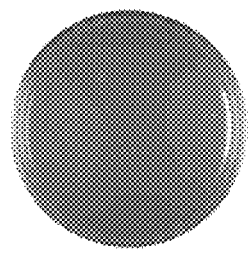
Figure 3:
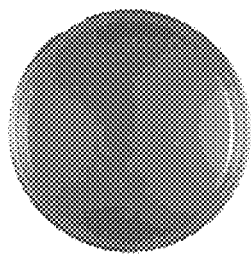
Figure 3:
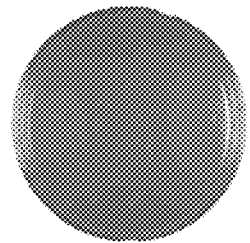
Figure 3:
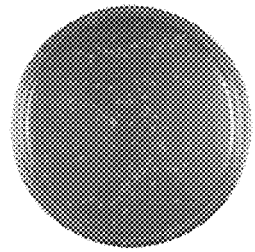
Figure 3:
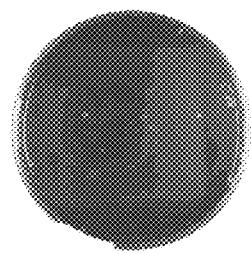
Figure 3:
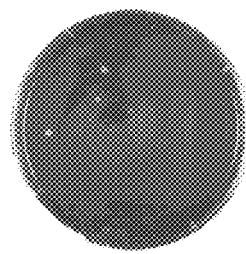
Figure 3:
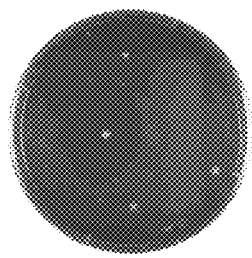
Figure 3:
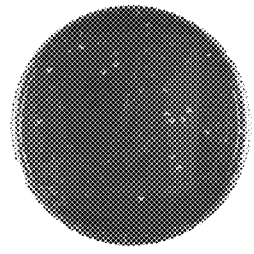
Figure 3:
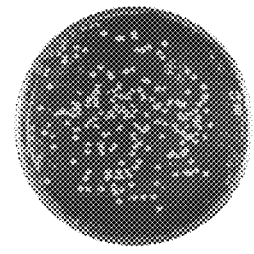

Not only did the boosted sera display excellent binding capacity against Ab-54149, it also led to apparent killing of live Ab-54149, H. pylori 26695, and P. aeruginosa PAO1 via bactericidal assay (FIG. 2, panel A, and FIG. 3). Remarkably, although Ab-SK44 EPS and Ab-54149 EPS shared most sugar components except for Pse, yet the fact that Ab-SK44 EPS was not recognized by the boosted serum suggested that Pse played a critical role in antigenicity. The boosted sera failed in recognition while the Pse on Ab-54149 EPS and ΦAB6TSP-digested product was diminished, confirming the importance of Pse (FIG. 2, panel B). Most strikingly, boosted serum particularly bound to Pse monosaccharide that was released from Ab-54149 EPS via mild acetic acid hydrolysis over time rather than other components on Ab-54149 EPS, including sialic acid, GalN Acp, Galp and Glcp (FIG. 2, panel C). Thus, it was reasonably to conclude that the specificity of antibodies recognition was attributed to the major structural differences between Pse and sialic acid of the N-acetyl group on C7 and the hydroxyl group on C9 with opposite chirality of C5, C7 and C8.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A glycoconjugate vaccine having the structure of formula (I),

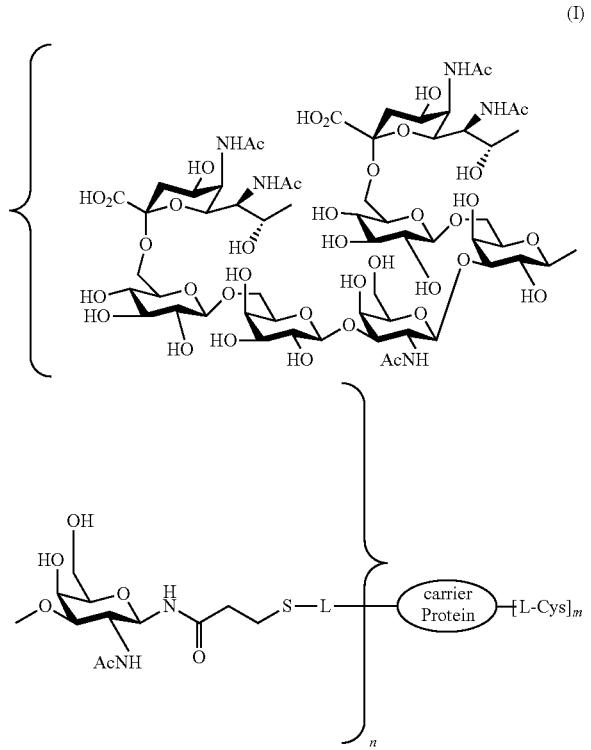

(I)

wherein,

L is a maleimide-type linker, which is connected to the carrier protein via a maleimide bond formed therebetween; and n consists of an integral of non-integral number of 2-10, and m consists of an integral or non-integral number of 10-19.

2. The glycoconjugate vaccine of claim 1, wherein the maleimide-type linker is selected from the group consisting of maleimidocaproyl (mc), maleimidomethyl cyclohexane-1-carboxylate (mcc), and succinimidyl 3-(bromoacetamido) propionate (SBAP).

3. The glycoconjugate vaccine of claim 2, wherein the carrier protein is selected from the group consisting of diphtheria toxin (DT) mutant of *Corynebacterium diphtheriae* 197 (CRM197), exototxin A of *P. aeruginosa* (EPA), diphtheria toxoid, tetanus toxoid, detoxified hemolysin A of *S. aureus*, clumping factor A, *E. coli* heat labile enterotoxin, detoxified variants of *E. coli* heat labile enterotoxin, Cholera toxin B subunits (CTB), cholera toxin, detoxified variants of cholera toxin, *C. jejuni* AcrA, and *C. jejuni* natural glycoproteins.

4. The glycoconjugate vaccine of claim 3, wherein in the formula (I), the maleimide-type linker is maleimidocaproyl, the carrier protein is the DT mutant of CRM197.

5. The glycoconjugate vaccine of claim 1, further comprising an adjuvant.

6. A method for the production of a glycoconjugate vaccine of formula (I) comprising:
  (a) digesting exopolysaccharides (EPS), isolated from a bacterium, with a phage tailspike protein (TSP) to produce an oligosaccharide (1);
  (b) treating the oligosaccharide (1) with ammonium carbonate to convert the free hydroxyl group on the GalNAc ring of the oligosaccharide (1) into a primary amine and subsequently with a sulfhydryl group introducing agent thereby generating an oligosaccharide (2) having a sulfhydryl group;
  (c) coupling the oligosaccharide (2) to a carrier protein having a plurality of maleimide-type linkers via a maleimide reaction that occurred between the sulfhydryl group of the oligosaccharide (2) and the maleimide group of the plurality of maleimide-type linkers of the carrier protein; and
  (d) quenching the maleimide reaction of the step (c) by the addition of a sufficient amount of a cysteine thereby generating the glycoconjugate vaccine of formula (I);

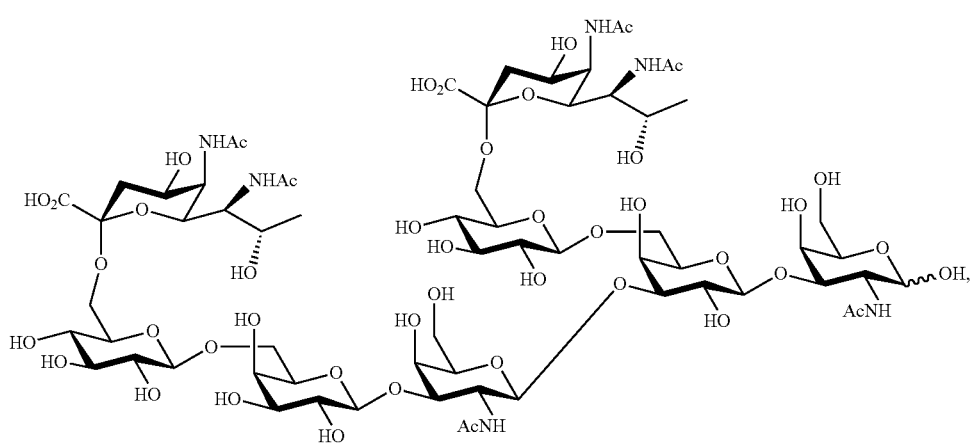

1

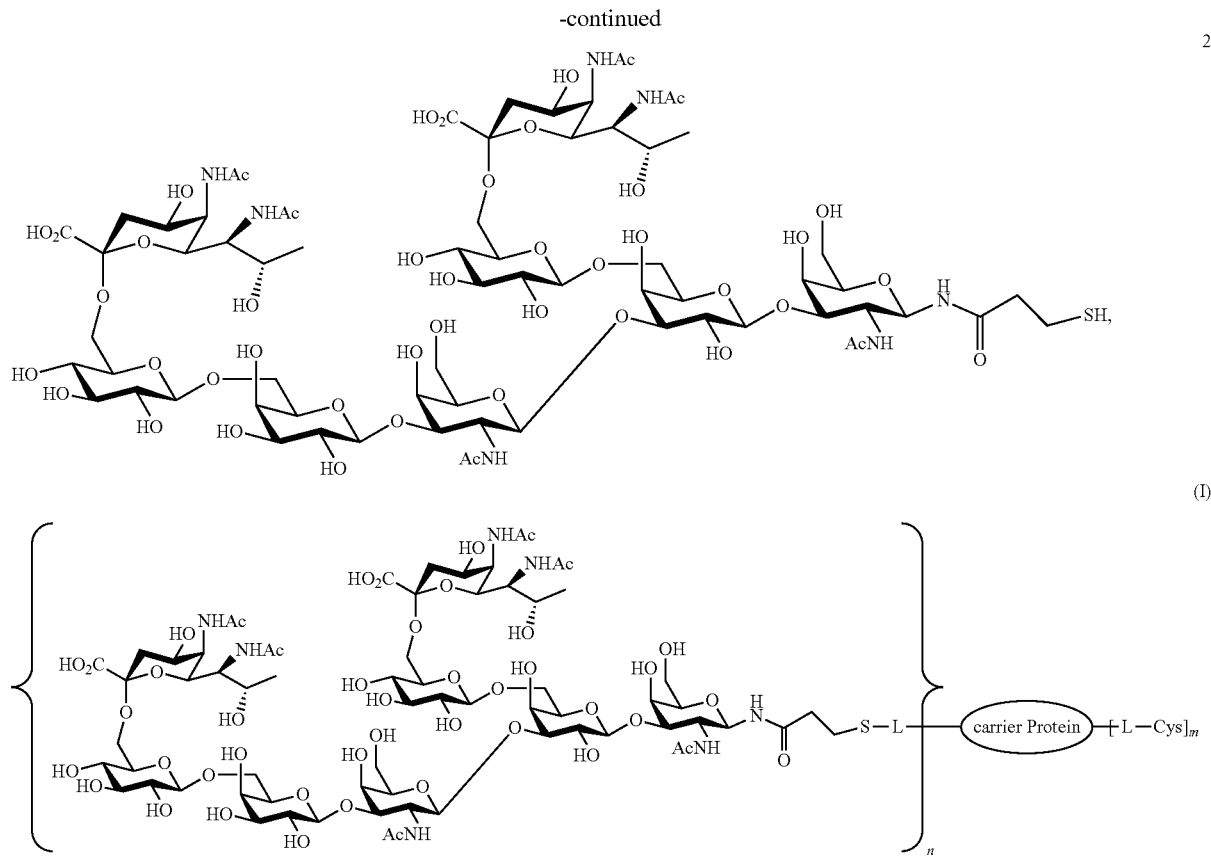

wherein,

L is the maleimide-type linker, which is connected to the carrier protein via a maleimide bond formed therebetween; and n consists of an integral or non-integral number of 2-10, and m consists of an integral or non-integral number of 10-19.

7. The method of claim 6, wherein in the step (a), the EPS is isolated from *Acinetobactor baumannii* strain 54149 (Ab-54149).

8. The method of claim 6, wherein in the step (a), the phage TSP is selected from the group consisting of phage AB6 TSP, phage P22 TSP, Phage SF6 TSP, Phage HK620 TSP, Phage T4 TSP and Phage T7 TSP.

9. The method of claim 6, wherein in the step (b), the sulfhydryl group introducing agent is 3,3-dithiobis(sulfosuccinimidylpropionate) (DTSSP), dithiobis[succinimidylpropionate] (DSP), 2-iminothiolane, N-succinimidyl S-acetylthioacetate (SATA), N-succinimidyl S-acetylthiopropionate (SATP), or N-succinimidyl S-acetylthiotetraethylene glycol (SAT(PEG)$_4$).

10. The method of claim 6, wherein in the formula (I), the maleimide-type linker is selected from the group consisting of maleimidocaproyl (mc), maleimidomethyl cyclohexane-1-carboxylate (mcc), and succinimidyl 3-(bromoacetamido) propionate.

11. The method of claim 10, wherein the carrier protein is selected from the group consisting of diphtheria toxin (DT) mutant of *Corynebacterium diphtheriae* 197 (CRM197), exototxin A of *P. aeruginosa* (EPA), diphtheria toxoid, tetanus toxoid, detoxified hemolysin A of *S. aureus*, clumping factor A, *E. coli* heat labile enterotoxin, detoxified variants of *E. coli* heat labile enterotoxin, Cholera toxin B subunits (CTB), cholera toxin, detoxified variants of cholera toxin, *C. jejuni* AcrA, and *C. jejuni* natural glycoproteins.

12. The method of claim 11, wherein in the formula (I), the maleimide-type linker is maleimidocaproyl, the carrier protein is the DT mutant CRM197.

13. A method of protecting a subject from being infected by a bacterium, comprising administering to the subject an effective amount of the glycoconjugate vaccine of claim 1, wherein the bacterium is any of *Acinetobactor baumannii* 54149, *Actinoplanes utahensis* VKM Ac-674, *Aeromonas caviae* UU51, *Campylobacter jejuni* 81-176, *Campylobacter jejuni* 11168, *Campylobacter coli* VC167, *Cellulophaga funcicola*, *Escherichia coli* O136, *Helicobacter pylori* 1061, *Helicobacter pylori* 26695, *Helicobacter pylori* 11687, *Kribbella* spp. VKM, *Piscirickettsia salmonis*, *Proteus vulgaris* O39, *Pseudomonas aeruginosa* O7a, *Pseudomonas aeruginosa* O7b, *Pseudomonas aeruginosa* O7d, *Pseudomonas aeruginosa* O9a, *Pseudomonas aeruginosa* O9b, *Pseudomonas aeruginosa* O10a, *Pseudomonas aeruginosa* PAO1, *Pseudomonas aeruginosa* PA14, *Pseudomonas atlantica* LAM 14165, *Pseudomonas atlantica* T9, *Pseudoalteromonas distincta* KMM 638, *Rhizobium* sp. NGR234, *Shigella boydii* type 7, *Sinorhizobium fredii* HH103, *Sinorhizobium meliloti* Rm1021, *Vibrio cholera* O:2, *Vibrio vulnificus* YJ016, or *Vibrio vulnificus* 27562.

14. A method of treating a bacterial infection in a subject, comprising administering to the subject an effective amount of the glycoconjugate vaccine of claim 1, wherein a bacterium is any of *Acinetobactor baumannii* 54149, *Actinoplanes utahensis* VKM Ac-674, *Aeromonas caviae* UU51, *Campylobacter jejuni* 81-176, *Campylobacter jejuni* 11168,

*Campylobacter coli* VC167, *Cellulophaga funcicola, Escherichia coli* O136, *Helicobacter pylori* 1061, *Helicobacter pylori* 26695, *Helicobacter pylori* 11687, *Kribbella* spp. VKM, *Piscirickettsia salmonis, Proteus vulgaris* O39, *Pseudomonas aeruginosa* O7a, *Pseudomonas aeruginosa* O7b, *Pseudomonas aeruginosa* O7d, *Pseudomonas aeruginosa* O9a, *Pseudomonas aeruginosa* O9b, *Pseudomonas aeruginosa* O10a, *Pseudomonas aeruginosa* PAO1, *Pseudomonas aeruginosa* PA14, *Pseudomonas atlantica* LAM 14165, *Pseudomonas atlantica* T9, *Pseudoalteromonas distincta* KMM 638, *Rhizobium* sp. NGR234, *Shigella boydii* type 7, *Sinorhizobium fredii* HH103, *Sinorhizobium meliloti* Rm1021, *Vibrio cholera* O:2, *Vibrio vulnificus* YJ016, or *Vibrio vulnificus* 27562.

15. The method of claim 14, further comprising administering to the subject at least one anti-bacterial agent selected from the group consisting of amoxicillin, ampicillin, azithromycin, clavulanic acid, cefuroxime, cefixime, cefpodoxime, ceftriaxone, doxycycline, luoroquinolones, macrolides, and moxifloxacin.

\* \* \* \* \*